United States Patent [19]
Ythier et al.

[11] Patent Number: 5,925,344
[45] Date of Patent: Jul. 20, 1999

[54] PHARMACEUTICAL COMPOSITION AND USES THEREFOR

[75] Inventors: Armaud Ythier, Collex Bossy, Switzerland; Jean-Claude Mestries, Berwin, France; Francis Herodin, Crolies, France; Serge Martin, Chewin de Craponoz, France

[73] Assignee: Applied Research Systems ARS Holdings NV, Netherlands

[21] Appl. No.: 08/367,124

[22] PCT Filed: Jul. 8, 1993

[86] PCT No.: PCT/EP93/01790

§ 371 Date: Mar. 3, 1995

§ 102(e) Date: Mar. 3, 1995

[87] PCT Pub. No.: WO94/01123

PCT Pub. Date: Jan. 20, 1994

[30] Foreign Application Priority Data

Jul. 8, 1992 [GB] United Kingdom ............... 9214489
Jan. 22, 1993 [GB] United Kingdom ............... 9301251

[51] Int. Cl.$^6$ .................................................. A61K 45/05
[52] U.S. Cl. ............................ 424/85.2; 530/351; 514/8; 514/12
[58] Field of Search ............................... 424/85.2; 514/8, 514/12; 530/351

[56] References Cited

U.S. PATENT DOCUMENTS 5,087,448 2/1992 Burstein .
5,188,828 2/1993 Goldberg et al. ................... 424/85.2
5,264,209 11/1993 Mikayama et al. .

FOREIGN PATENT DOCUMENTS 0363083 4/1990 European Pat. Off. .
0378171 7/1990 European Pat. Off. .
9002570 3/1990 WIPO .
9208493 5/1992 WIPO .
9306840 4/1993 WIPO .

OTHER PUBLICATIONS

"Induction of Rat Acute–Phase Proteins by Interleukin 6 *In Vivo*"; Thomas Geiger, Tilo Andus, Jan Klapproth, Toshio Hirano, Tadamitsu Kishimoto and Peter C. Heinrich; *Eur. J. Immunol.*; 1988.18: 717–721.

"Human Endothelial Cells Produce IL–6—Lack of Responses to Exogenous IL–6$^a$"; Thomas J. Podor, Frank R. Jirik, David J. Loskutoff, Dennis A. Carson and Martin Lotz; Annals New York Academy of Sciences; 557, 374–85; 1989.

"Dexamethasone and Phorbol Ester, but not Cytokines, Increase the Production of Plasminogen Activator Inhibitor Type–2 in the PL–21 Human Promyeloctyc Leukemia Cell Line"; Kenji Niiya, Tetsuo Takeuchi, Makoto Kobayashi, Isao Miyoshi, Tomohiro Hayashi and Nobuo Sakuragawa; Thrombosis and Haemostasis; 66(2), 232–238; 1991.

"Human HuH–7 Hepatoma Cells Express Urokinase and Plasminogen Activator Inhibitor–1; Identification, Characterization and Regulation by Inflammatory Mediators"; Allan Arndt, Patricai Murphy and David A. Hart; *Biochim. et Biophys. Acta*; 1138, 149–156; Feb. 14, 1992.

"Type 1 Plasminogen Activator Inhibitor is not an Acute Phase Ractant in Rats—Lack of IL–6 and Hepatocyte–Dependent Synthesis"; Thomas J. Podor, Jack Hirsh, Thomas D. Gelehrter, Ron Zeheb, Diane Torry, Yves Guigoz, Felipe Sierra and Jack Gualdie; *J. Immunology*; 150(1), 225–235; Jan. 1, 1993.

J. V. Castell et al., "Recombinant Human Interleukin–6 (IL–6/BSF–2/hsf) Regulates the Synthesis of Acute Phase Proteins in Human Hepatocytes", FEBS Letters, vol. 232, No. 2, May 1988, pp. 347–350.

"The Merck Manual of Diagnosis + Therapy" (vol. I, General Medicine Merck + Co., (1987).

P. Wolf, "The importance of Azpha(2)–Antiplasminin in The Defibrination Syndrome" Arch. Intern. Medicine vol. 149, Aug. 1989.

*Primary Examiner*—Johann Richter
*Assistant Examiner*—Patrick R. Delaney
*Attorney, Agent, or Firm*—Ostrolenk, Faber, Gerb & Soffen, LLP

[57] ABSTRACT

The invention provides use of interleukin-6 in the manufacture of a medicament for the treatment or prophylaxis of consumptive thrombohemorrhagic disorder. The invention also provides use of interleukin-6 in the manufacture of a medicament for the treatment or prophylaxis of a dysfunction associated with a reduced level of at least one acute phase protein.

9 Claims, 11 Drawing Sheets

PHARMACEUTICAL COMPOSITION AND USES THEREFOR

This is a 371 of PCT/EP93/01790 filed Jul. 8, 1993

This invention relates to the novel use of certain cytokines in the treatment of certain blood disorders, primarily consumptive thrombohemorrhagic disorder.

Consumptive thrombohemorrhagic disorder comprises disseminated intravascular coagulation (DIC), defibrination syndrome and consumptive coagulopathy. A consumptive thrombohemorrhagic disorder is a pathological syndrome, the manifestation of which can in large part be regarded as a consequence of thrombin formation although other features such as blood factor and platelet consumption and fibrinolysis are present. Thrombin catalyses the activation and subsequent consumption of certain coagulant proteins and production of fibrin thrombi or clots. The fibrin thrombus is seen as an indicator of DIC. Microvascular, non adherent thrombi are present in almost all cases of DIC.

The symptoms of consumptive thrombohemorrhagic disorder such as DIC vary with the stage and severity of the consumptive thrombohemorrhagic disorder. Most patients have extensive skin and mucous membrane bleeding and hemorrhage from multiple sites. Occasionally patients have abnormalities in laboratory tests without clinical manifestations. The major manifestations in laboratory tests include thrombocytopenia, prolonged prothrombin time (PT), activated partial thromboplastin time (APTT) and thrombin time (TT) and a reduced fibrinogen plasma level illustrating the consumption of essential coagulation factors. Elevated fibrin degradation products (FDPs or fibrin split products) account for intense secondary fibrinolysis. Other factors such as factors V, VIII and XIII are usually decreased. Such findings can strengthen the diagnosis.

In particular, lowered factor VIII levels may be a sensitive indicator. However, the major manifestation of DIC, which correlates closely with bleeding, is the reduced plasma fibrinogen level. Normally, there is a fine balance in blood between clot-forming and clot-dissolving factors as will be explained in more detail below.

Heretofore, the treatment of consumptive thrombohemorrhagic disorder has been based on the correction of any reversible cause of consumptive thrombohemorrhagic disorder, on measures to control the major symptoms i.e. bleeding and/or thrombosis, and on prophylactic regimens to prevent recurrence of the causes. Treatments vary according to the cause and the clinical presentation but the major issue is the control of bleeding and thrombosis which are often associated. Accordingly, the clinician may supply the patients with plasma coagulation factors, attempt to correct the hypofibrinogenemia and correct the thrombocytopenia by infusing fresh frozen plasma as well as platelet concentrates. Thrombosis is normally counteracted by the administration of heparin, which is a potent antithrombin agent capable of preventing further consumption of coagulation factors. Agents which inhibit the associated fibrinolysis are rarely used because of the difficulty in controlling their secondary thrombotic effects.

Care has to be exercised over the timing of administration of heparin and blood products. Transfusion without prior administration of heparin may actually promote thrombosis without correcting the plasma deficiency state. The clinician has to overcome the paradox of administering an anticoagulant to a patient with bleeding manifestations. Logic dictates that bleeding would be worsened initially by the additive effect of heparin. Once heparin treatment has been instituted, bleeding diathesis needs to be immediately treated by replenishing the depleted (consumed) supply of platelets and clotting factors.

Clearly, there is a need for a relatively simple regimen for the treatment of consumptive thrombohemorrhagic disorder in which the clinician is not faced with the task of balancing the patient's requirements for several substances in order to restore normal hemostasis.

Surprisingly, we have discovered that the administration of interleukin-6 (IL-6) can be used beneficially in combatting consumptive thrombohemorrhagic disorder such as DIC in that it not only increases blood platelet count but simultaneously elevates the level of plasma fibrinogen and inhibits fibrinolysis and thrombin formation. It also induces an elevation of plasma acute phase proteins, such as alpha-1 antitrypsin and alpha-2 macroglobulin which are known natural inactivators of plasmin and thus inhibitors or fibrinolysis.

One aspect of the present invention provides use of interleukin-6 in the manufacture of a medicament for the treatment or prophylaxis of consumptive thrombohemorrhagic disorder, preferably disseminated intravascular coagulation.

The invention further includes a method of treatment or prophylaxis of a human or animal subject suffering from or at risk to consumptive thrombohemorrhagic disorder, preferably disseminated intravascular coagulation wherein an effective dose of interleukin-6 is administered to said subject.

Also, the invention additionally provides use of IL-6 in the manufacture of a medicament for the treatment or prophylaxis of a dysfunction associated with a reduced level of at least one plasma acute phase protein.

This use of IL-6 is ideally suited to the management of DIC since it not only meets the requirements stated above but also increases the blood platelet count.

The expression "interleukin-6" and the term "IL-6" are both intended to encompass natural, synthetic and recombinant forms of the polypeptide as well as derivatives thereof. IL-6 has been characterised and discussed for example in M. Revel, Experientia 54: 549–557 (1989). Preferably, recombinant human IL-6 (hrIL-6) is used.

DIC is mainly observed in obstetric complications, metastatic malignancies, massive trauma, and bacterial sepsis. Causes of DIC can be classified according to the initiating mechanism and fall into four groups:

1) Liberation of tissue factors in for example i) obstetric syndromes such as abruptio placentae, amniotic fluid embolism, retained dead foetus and second trimester abortion; ii) hemolysis; iii) neoplasms such as mucinous adenocarcinomas and acute promyelocytic leukemia; iv) intravascular hemolysis; v) fat embolism; and vi) tissue damage such as, for example, burns, head injury, gunshot wounds, surgical trauma and snake bites;

2) Endothelial damage in for example aortic aneurysm, haemolytic uraemic syndrome, and acute glomerulonephritis;

3) Vascular malformations and decreased blood flow which are typically found in the Kasabach-Merrit syndrome; and 4) Infections (particularly when accompanied by septic shock), the causative agents of which may be bacterial e.g. staphylococcal, streptococcal, pneumococcal, meningococcal or gram negative bacilli; fungal, e.g. Aspergillus, *Candida albicans;* viral, e.g. arboviruses, varicella, variola or rubella; parasitic, particularly malaria and kala-azar; rickettsial e.g. Rocky Mountain spotted fever or mycotic e.g. acute histoplasmosis. Thus, interleukin-6 may be used to treat septic shock associated with consumptive thrombohemorrhagic disorders.

DIC is a life threatening syndrome and clinically, has been divided into the following four syndromes:

a) Compensated DIC, which may be associated with thrombosis but does not result in bleeding;

b) Defibrination syndrome, in which the mechanisms that localize blood coagulation are overwhelmed by release of tissue factors, leading to massive utilization and depletion of fibrinogen, other clotting factors, and platelets leading to thrombosis and/or bleeding;

c) Primary fibrinolysis, in which the mechanisms that localise fibrinolysis are overwhelmed by release of plasminogen activators, leading to bleeding; and d) Microangiopathic thrombocytopenia, in which platelet microthrombi are widespread, leading to depletion of platelets, ischemic necrosis of tissues, and microangiopathy changes in red cells.

The initial stages of DIC may not be readily apparent to the clinician because, for example, the cause of DIC, e.g. infection, may mask the early stages in the course of the disorder. However, the disorder may gain momentum rapidly and assume importance beyond that of the initiating stimulus.

Intrinsic and extrinsic coagulation systems are activated in DIC with resulting local and general escape of thrombin into the circulatory system. Alterations of any of the components of the vascular system, namely vessel wall, plasma proteins, and platelets, can result in a consumptive disorder. Endothelial damage, as mentioned above relates to those disease states which specifically injure the endothelium, with resultant kallikrein-kinin activation i.e. intrinsic coagulation. Tissue injury on the other hand liberates tissue factors and refers to those disease states in which procoagulant material, e.g. tissue thromboplastin, acts locally or is released into the circulation i.e. extrinsic coagulation. The intrinsic and extrinsic coagulation systems lead to the formation of an enzymic complex (factor Xa, factor V, calcium and phospholipids), which transforms prothrombin (factor II) into thrombin.

The consumptive processes of DIC reflect the multiple actions of thrombin. Thrombin proteolytically cleaves fibrinopeptides from fibrinogen to produce fibrin monomers which either combine with fibrinogen to form soluble complexes or polymerize to form fibrin thrombi. The fibrin thrombi often cause microvascular occlusions which lead to local hypoperfusion, and even ischemia, infarction and necrosis. The fibrin formation initiated by thrombin decreases plasma fibrinogen concentration. Thrombin also activates factor XIII, which renders fibrin more resistant to fibrinolysis and therefore lowers the likelihood of thrombi dissolution. Moreover, thrombin binds to platelets at low concentration and initiates shape change, aggregation, and secretion. The platelet contribution to prothrombin activation into thrombin is partly due to platelet factor V bound to platelet surface, which serves as a receptor for factor Xa. Thrombin stimulates platelets to release platelet factor V. In effect, thrombin potentiates the coagulation cascade, which leads to its formation by activating plasma coagulation factors V and VIII. By this mechanism thrombin activity accounts for the decrease in fibrinogen, platelets (thrombocytopenia), and coagulation factors II, V, VIII and XIII. Typically, a normal thrombin time in humans is 9–13±3 seconds.

It is known that the prothrombotic activity of thrombin is neutralised by two natural inhibitory systems, which are dependent upon the interaction of plasma proteins with the endothelial surface. Antithrombin III and heparin cofactor II both neutralize thrombin slowly by complex formation. However such neutralisation is enhanced in the presence of heparin.

Plasmin is a potent proteolytic enzyme capable of digesting fibrin and fibrinogen as well as other clotting proteins, including factors V and VIII. Plasmin, in response to the presence of fibrin thrombi, minimizes the vascular obstructive and ischemic effects of consumption. Plasmin is formed from plasminogen by plasminogen activators such as tissue plasminogen activator (t-PA), which activators are located in neutrophils and in the endothelium blood vessels and are released in case of tissue injury. Plasmin formation and fibrinolysis are localised to the fibrin clot by a number of fibrinolysis inhibitors one of which is plasminogen activator inhibitor-1 (PAI-1). Plasmin formation also occurs in the presence of activated factor XII and/or kallicrein e.g. contact phase of the intrinsic coagulation system. Thus fibrinolysis is initiated when thrombin formation is induced, whether it is triggered by contact i.e. intrinsic coagulation system or by tissue injury i.e. extrinsic coagulation system. The balance between these two proteases, i.e. thrombin and plasmin, determines whether the clinical picture is characterized by thrombosis, organ ischemia and bleeding (thrombin predominance) or predominantly by bleeding (thrombin and plasmin action). Alpha-1 antitrypsin as well as alpha-2 macroglobulin naturally inactivate plasmin. Both alpha-1 antitrypsin and alpha-2 macroglobulin are acute phase proteins and others of the group include C3c complement, transferrin, haptoglobulin acid $\alpha$-1 glycoprotein, ceruloplasmin and C-reactive protein.

The involvement of IL-6 in fibrinolysis is further demonstrated by our observation that on injection of IL-6, both tissue plasminogen activator (t-PA) and plasminogen activator inhibitor (PAI-1) are released. This suggests stimulation by IL-6 of the endothelial cells. t-PA levels rise about four fold, which is within the range observed in healthy subjects, for example after exercise, but the rise in PAI-1 levels is about 30-fold.

It will be clear from the foregoing that it is desirable in the management of DIC to increase the blood platelet count, elevate the plasma fibrinogen level, induce a prolonged thrombin time and increase inhibitors of fibrinolysis and fibrinogenlysis (alpha-2 macroglobulin and alpha-1 antitrypsin which are plasma acute phase proteins); all of which are produced by administration of IL-6.

Medicaments comprising IL-6 may be administered by the oral, rectal, intranasal, transdermal and parenteral routes, the latter being preferred. The proposed dosage is preferably 35 to 350 $\mu$g of active substance per dose, low doses being appropriate for infusion or injection and higher doses being appropriate for other forms of administration. The recommended dose for intravenous application is from 0.5 to 30 $\mu$g/Kg/day, preferably from 1 to 10 $\mu$g/Kg/day. Where the active substance is administered gradually, for example by infusion, the rate of administration is preferably from 0.02 to 1.25 $\mu$g/kg/hour, more preferably 0.04 to 0.4 $\mu$g/kg/hour. Delayed release oral forms should desirably release the active substance at about this dose rate.

Suitable forms of administration include tablets, capsules, suppositories, solutions, syrups, emulsions, aerosols and dispersible powders. Suitable tablets may be prepared, for example, by mixing the active substance or substances with known adjuvants, for example inert diluents such as calcium carbonate, calcium phosphate or lactose, disintegrants such as corn starch or alginic acid, binders such as starch or gelatine, lubricants such as magnesium stearate or talc and/or agents for obtaining delayed release such as carboxypolymethylene, carboxymethylcellulose, cellulose acetate phthalate or polyvinyl acetate. The tablets may also consist of several layers.

Coated tablets may be prepared in the same way by coating cores produced analogously to the tablets with substances conventionally used for tablet coating, e.g. collidone or shellack, gum arabic, talc, titanium dioxide or sugar. In order to obtain delayed release or prevent intolerance, the core may also consist of several layers. Similarly, the table coating may consist of several layers in order to achieve delayed release, using the excipients given above for the tablets.

In order to avoid degradation of the active polypeptide by gastric acids, tablets may be provided with an enteric coating which is insoluble at the pH in the stomach but dissolves at the pH of the intestine e.g. pH 6.0 or greater. Suitable coating materials include polymethylmethacrylates such as Eudragit (Röhm, Darmstadt).

Syrups of the active substances or combinations of active substances according to the invention may additionally contain a sweetener such as saccharin, cyclamate, glycerine or sugar and a flavour-enhancing agent, e.g. a flavouring such as vanillin or orange extract. They may also contain suspension adjuvants or thickeners such as sodium carboxymethylcellulose, wetting agents, e.g. condensation products of fatty alcohols with ethylene oxide, or preservatives such as p-hydroxybenzoates.

Solutions for infusion or injection may be prepared in conventional manner, e.g. with the addition of preservatives such as p-hydroxybenzoates or stabilisers such as alkali metal salts of ethylene-diamine tetraacetic acid and may then be transferred into fusion vessels, injection vials or ampoules. Alternatively, the compound for injection may be lyophilised either with or without the other ingredients and be solubilised in a buffered solution or distilled water, as appropriate, at the time of use. Bolus intravenous injections may be given.

Capsules containing the active substances or combinations of active substances may be prepared, for example, by mixing the active substances with inert vehicles such as lactose or sorbitol and encapsulating them in gelatine capsules.

Suitable suppositories may be prepared, for example, by mixing with carrier substances provided for this purpose, such as neutral fats or polyethylene glycol or derivatives thereof.

The compound may be mixed with a polylactide or a glutamic acid based copolymer to provide an implantable sustained release delivery system, as described respectively in U.S. Pat. No. 377,919 and by K. R. Sidman et al (J. Membrance Sci. 1980 7 277–291).

The invention will now be described by way of illustration only with reference to the following Examples and Figures.

In all figures, the closed circles represent the IL-6 treated baboons and the open circles represent the control baboons.

EXAMPLE 1

Material and Methods rhIL-6

The recombinant human IL-6 (rhIL-6) used was produced by expressing a complementary DNA for human IL-6 in the mammalian cell CHO. A single production batch was used for the entire study. The physiochemical characterisation showed that the amino acid composition of the rhIL-6 is consistent with the theoretical one deduced from the coding gene. Glycosylation of the molecule takes place at N- and O-glycosylation sites. Purity was superior to 99%. Endotoxin content was under measurable limits. Specific activity was at $13.7 \cdot 10^6$ units/mg of protein.

Recombinant hIL-6 was stored frozen in solution at −20° Celsius in PBS, pH 7, in aliquots of 1.1 ml at a concentration of 200 or 400 μg/ml. In these conditions, rhIL-6 was stable for several months. Dilutions for injection were extemporary prepared in sodium chloride containing 1% of baboon serum.

Animals 25 baboons (22 males, 3 females), weighing 20 to 25 kg were quarantined on arrival and screened for evidence of disease before being released from quarantine. They were housed individually and were fed with commercial primate food and fresh fruits and had an automatic tap water dispenser ad libitum.

Irradiation

One group of baboons underwent a total body exposure to mixed neutron-gamma radiation in order to induce bone-marrow depression.

Hermatological Examinations

Blood samples were drawn under general anaesthesia (ketamine 5 mg/kg) from the posterior saphena vein. Complete blood cell counts (WBC, RBC, hematocrit, hemoglobin) were performed using a Coulter counter equipped with a veterinary kit and differential white blood cell counts were performed on smear preparations stained with May-Grünwald-Giemsa.

Blood Chemistry

A variety of blood chemistry tests were performed, which monitored, for example, acute phase proteins such as α1-antitrypsin, and α2-macroglublin.

Haemostasis was monitored inter alia by activated partial thromboplastin time (APTT or kaolin-cephalin time), thrombin time and fibrinogen quantative tests.

The kaolin-cephalin clotting time (or partial thromboplastin time (PTT) and APTT) was used to evaluate the intrinsic system. This is a clotting time of plasma, free of $Ca^{++}$ and poor in platelets, in the presence of cephalin (a substitute for platelet factor III extracted from tissue) and of kaolin (a clay-like substance) that activates under standardized conditions factor XIII. The test is then a measure of factors XII, XI, X, IX, VIII, V, II and I. The normal activated partial thromboplastin time in baboons is of the order of 35 seconds.

Thrombin time was determined on the basis that normal plasma clots in a definite and constant time in the presence of a known quantity of thrombin. The thrombin time is longer in case of hypofibrinogenemia and if there is anti-thrombin in plasma.

The quantitative assay for fibrinogen uses a clotting time of a diluted plasma in the presence of an excess of thrombin. The time required to clot is directly related to the amount of plasmatic fibrinogen.

Clinical Examinations

Physical inspection, rectal temperature, weight, food intake, behaviour, injection site observations, were performed twice daily during the whole study follow up period. Further inspections of health conditions took place regularly under the supervision of the responsible investigator beyond the study follow up time.

An initial dose finding study to assess the efficacy and tolerance of rhIL-6 was performed on 10 normal baboons (7 males and 3 females), weighing between 20 and 25 kg.

Out of five groups of two individuals, four respectively received 20, 10, 3, 1 µg/kg/day of rhIL-6 in two daily subcutaneous injections for 8 consecutive days. The control group received the vehicle only according to the same schedule.

The study was performed in two subsequent sessions, the first one assessed the two highest dose groups and one subject as control, the second one assessed the two lowest dose groups and another subject as control. An additional monkey was incidentally given a single rhIL-6 s.c. injection of 10 µg/kg during the second session. This unique administration induced a significant platelet count increase four days after the injection. Blood sampling for hematologic examinations was performed at 1, 3, 6, 24 hours after the first rhIL-6 injection, then every day during the treatment period and then twice weekly up to 37–40 days post treatment onset. For the two highest dose groups and their control additional blood samples were collected for the assessment of several biochemical and hemostasis parameters, which induced a substantial blood loss.

Based on the hematopoietic effects, especially on thrombopoiesis, induced by rhIL-6 on normal monkeys, a second study was initiated to evaluate the ability of rhIL-6 to accelerate haematopoiesis regeneration following radiation induced haematopoietic injury. Fourteen new male baboons weighing between 20 and 25 kg were randomly allocated to three groups. One group of 6 irradiated subjects ("irradiated treated" group or IT) received 10 µg/kg/day of rhIL-6 into two daily subcutaneous injections for 13 consecutive days. This dosage was deemed optimal based on efficacy and tolerance features generated during the preliminary dose finding study in normal monkeys. One group of 6 irradiated subjects ("irradiated non treated" group or INT) received the vehicle only in an identical schedule. One group of 2 subjects ("sham irradiated" group of NIT) received 10 µg/kg/day in an identical fashion and served as the rhIL-6 bioactivity control. All treatments (rhIL-6 or vehicle) always started one day (day 1) after the irradiation date (day 0).

Results in Non-irradiated Baboons Injected with IL-6

Clinical Tolerance

The follow up of clinical symptomatology was done every day for at least forty days after the onset of treatment. No significant modifications of body weight, food consumption, body temperature and behaviour were observed during the study duration. No signs of general or local (at the injection sites) intolerance were noted. No deaths in either group were recorded.

Hematological Examinations

Human recombinant IL-6 induced a significant increase in blood platelet count generally starting after 4 to 5 days of treatment for all doses tested. Time to the thrombocytosis varied from day 8 up to 13 after the treatment onset and was not related to dose. Although the number of individuals in each dose group was too small to perform a statistical analysis, a dose dependent response trend was observed up to 10 µg/kg/day for the maximum increase in platelet count. At 20 µg/kg/day, the maximum platelet elevation seemed to be blunt.

Hemostasis

The thrombin time increased in all treated baboons; un some of the treated animals it raised from 20 up to 35 seconds within the first week of treatment. The highest values were observed in the two animals treated with 20 µg/kg/day.

Fibrinogen increased more than four times in all treated baboons and peaked until the treatment end. This rapid increase was not proportional to the dose injected. A progressive normalisation started after treatment discontinuation.

Acute Phase Proteins

There was a clear increase in ceruloplasmin in all treated individuals as compared to the control which did not appear to be dose-dependent. There was a very progressive return to baseline values after treatment discontinuation.

There was a considerable increase in C-reactive protein in all treated baboons. Normalisation occurred between 2 and 12 days after the end of the treatment.

The clear increase in haptoglobulin in all animals with a very progressive normalisation after treatment discontinuation does not seem to be dose related.

Results in Induced Bone-marrow Depression

Clinical Tolerance

Typical post radiation syndrome was distributed in both study groups. No noticeable aggravation of these symptoms by rhIL-6 was observed. The two non-irradiated controls did not display any particular clinical symptomatology. No local intolerance was ever noticed at the injections sites. No death in either group was recorded during and after the study period.

Hematological Examinations

Recombinant hIL-6 significantly attenuated radiation induced thrombocytopenia and accelerated platelets recovery.

The neutronic irradiation induced a deep thrombocytopenia in both groups. The time to nadir defined as the number of days from day 0 to the nadir was significantly different with a mean time of 7.7 days±0.8 corresponding to 7 full day of rhIL-6 therapy in the treated group versus a mean time of 12.8 days±1.9 in the control group (p=0.003). Moreover, the mean time to return at least to the baseline value (calculated as the mean platelet count of the twelve baboons, before irradiation) was significantly shorter in the treated group, 17.3 days±5.2, verses 25.0±2.2 in the untreated group (p=0.003). There was a significant increase in platelet count above normal values (peak 559,000/mm$^3$, p=0.03) for a few days during the recovery phase of the irradiated treated animals compared to the spontaneous recovery slope of the non treated group. As expected, the "sham irradiated" treated controls displayed a considerable thrombocytosis, confirming the data observed during the dose finding study.

In contrast, rhIL-6 therapy neither attenuated the intensity of the radiation induced leukopenia nor accelerated its recovery.

Hemostasis

The thrombin time duration increased beyond normal values in groups receiving rhIL-6 (either IT or NIT). There was a statistically significant difference (in average from day 2 to day 14) between the IT and INT groups (see below):

| mean Thrombin Time (sec) | IT | INT |
| --- | --- | --- |
|  | 28.9 | 18.7 |

Progressive normalisation was observed after treatment discontinuation.

Activated Partial Thromboplastin Time (APTT)

A statistically significant prolongation (in average from day 2 to day 14) of the mean APTT was observed between the rhIL-6 treated (IT) and non treated animals (INT). A similar increase was observed in the "sham irradiated" group (NIT).

| mean APTT (sec) | IT | INT |
| --- | --- | --- |
|  | 50.9 | 39.7 |

Progressive normalisation occurred after treatment discontinuation.

Fibrinogen

All groups of animals displayed elevated mean fibrinogen values. However, a more dramatic elevation was seen in the animals receiving rhIL-6 (either IT or NIT). A statistically significant difference (in average from day 2 to day 14) was observed between the IT and INT groups (see below):

| mean Fibrinogen (g/l) | IT | INT |
| --- | --- | --- |
|  | 9.1 | 4.0 |

Progressive normalisation occurred after treatment discontinuation.

Acute Phase Proteins

C3c complement: there was a clear increase in the rhIL-6 treated groups (IT and NIT) with a progressive normalisation. Irradiation does not seem to influence the C3c complement circulating levels.

Ceruloplasmin: there was a clear increase in all treated animals as compared to the irradiated non-treated group (NIT), with a very progressive return to baseline values after treatment discontinuation.

C reactive protein: all groups of animals displayed a significant increase. However, this elevation was transient in the irradiated non-treated animals (INT), although it lasted during the whole rhIL-6 treatment period for the two other groups. Normalisation was rapidly occurring after treatment discontinuation.

Acid α-1-glycoprotein and Haptoglobulin: a clear increase was observed in animals receiving rhIL-6 (IT and NIT), followed by a progressive normalisation.

α-1-Antitrypsin: a clear increase was observed in animals receiving rhIL-6 (IT and NIT), followed by progressive normalisation.

α-2-Macroglobulin: an increase was observed in all groups of animals. The elevation was transient in the INT group, although it lasted during the whole rhIL-6 treatment period for the two other groups. Normalisation occurred rapidly after treatment discontinuation.

Haemostasis

The most striking feature is the prolongation of the thrombin time and to a lesser extent the duration increase of the APTT. The results suggest a disturbance of fibrin formation which may be linked to the considerable elevation of fibrinogen induced by rhIL-6 in these same animals. However, irradiated non rhIL-6 treated animals (INT) which also displayed a fibrinogen increase although less pronounced, did not show thrombin time perturbations.

It must be stressed that full normalisation of coagulation parameters as well as fibrinogen occurred after treatment discontinuation.

Blood Chemistry

Ceruloplasmin, C reactive protein, acid α-1-glycoprotein, haptoglobulin, α-1-antitrypsin, α-2-macroglobulin, C3c complement and fibrinogen were all significantly increased in all rhIL-6 treated animals. The most striking effects were however observed for fibrinogen and C reactive protein. All perturbations were reversible upon treatment discontinuation.

EXAMPLE 2

Materials and Methods

Interleukin 6

Recombinant glycosylated interleukin 6 was produced by expressing a complementary DNA for human interleukin 6 in chinese hamster ovary cells and was supplied by Ares Serono (Geneva, Switzerland). Its amino acid sequence, carbohydrate composition and carbohydrate attachment sites were identical to that of natural human IL-6. The specific activity of the preparation, as measured on murine T1165 plasmacytoma cells and using the IL-6 standard of the National Institute for Biological Standards and Control (Potters Bar, UK) was $12.7 \times 10^6$ U/mg. A single batch was used throughout the study. Endotoxin content as measured by the lumulus lysate test was below detection limit (<0.1 endotoxin units/mg).

Animals

Eight baboons (Papio ursinus; Cape Laboratories, Geneva, Switzerland) weighing 20 to 25 kg were quarantined for three months on arrival and screened for evidence of disease before being released from quarantine. They were housed individually in stainless steel cages in a facility accredited by the Ministry of Agriculture, Environment and Nature Preservation. Animal rooms were equipped with a reverse filtered air barrier and full spectrum light (8 am to 8 pm) and were conditioned to 23° C. with a relative humidity of 60%. They were fed with commercial primate chow and fresh fruits and tap water ad libitum. Animals were kept under anesthesia (Ketamine 7 mg/kg) during injection and at each blood collection.

Blood Collection

Blood was collected from the posterior saphenous vein by clean venepuncture and mixed in precooled tubes without anticoagulant for serum (acute phase proteins) or with anticoagulant (citrate (most assays) or citrate containing a protease inhibitor mixture for fibrinopeptide A or plasmin-antiplasmin complexes Stago).

Assays

All reagents and assay kits have been tested in preliminary experiments for their suitability to assay the respective parameters in baboons.

Coagulation Assays

The routine overall coagulation tests: the prothrombin time, the activated partial thromboplastin time and the thrombin time tests were performed using reagents obtained from Diagnostica Stago (Asnieres, France). Functional antithrombin III concentrations were measured by a chromogenic substrate technique (Stachrom ATIII, Diagnostica, Stago) and antigen concentrations by nephelometry (Behring, Frankfurt, Germany). Prothrombin fragment 1+2 concentrations were quantified by ELISA (enzygnost 1+2, Behring). Fibrinopeptide A concentrations were measured in plasma after removal of fibrinogen by bentonite adsorption using a competitive enzyme-linked immunoassay (Asserachrom FPA, Diagnostica, Stago). Thrombin-antighrombin III complex concentrations were determined by ELISA (enzygnost TAT micro, Behring). D-dimer concentrations were determined by ELISA (Asserachrom D-Di, Stago) Factor X, Factor II and PC, assay description. Factor Xa activity was calculated as 1/t and expressed in percent of initial values.

Fibrinolytic Factors

Antigen concentrations of the fibrinolytic factors were measured by immunoassays: t-PA using the Tintelize t-PA kit (Biopool, Umea, Sweden); PAI-1 using the PAI-1 ELISA kit (Monozyme, Virum, Denmark) and plasmin-antiplasmin complexes using the PAP ELISA kit (Technoclone, Vienna, Austria).

Interleukin 6 concentrations were measured by ELISA (Immunotech, Marseille, France).

Acute Phrase Response Proteins

Antigen concentrations of C-reactive protein, haptoglobin, alpha-2-macroglobulin, alpha-1-antitrypsin, alpha-1-acid glycoprotein (orosomucoid), prealbumin and fibronectin were measured by nephelometry using a BNA nephelometer and specific antisera provided by Behring.

Study Design

An initial dose finding study was performed using five baboons receiving a single subcutaneous injection of rh-IL-6 at doses of 0, 5, 30, 100 and 500 µg of per kg body weight, based upon the results of the dose finding study a dose of 100 µg/kg was selected. Four baboons received a single subcutaneous injection of 100 µg/kg of rh-IL-6 in sterile 0.9% NaCl containing 1% of baboon serum and four baboons received vehicle only. During the study the animals were examined daily for changes in body weight, behaviour, food intake and body temperature. Blood was collected (17 ml per occasion) before and 30 min, 1 h, 3 h, 6 h, 8 h and 24 h after injection, then once every day during 7 days and two times during the second week. Blood samples were stored at −80° C. until assay (which was performed within 1 month).

Results

Effect of a Single Subcutaneous Injection of rh-IL-6 on Clinical and Hematological Parameters No significant modifications of body weight, food consumption, body temperature or behaviour, signs of general or local (at the injection site) intolerance nor clinical signs of coagulation disorders were observed. No animal loss was recorded in either group. In IL-6 treated baboons platelet counts started to increase after 2–3 days and a maximal increase of 65% was observed around day 7. Variations of platelet counts in the control group were minimal. Hematocrit and hemoglobin values decreased in both the vehicle and IL-6 treated baboons to a minimum of 85% of pre-injection values, which was attained at day 4 to 7 and normalized thereafter.

Interleukin 6 Concentrations

Figure 1:
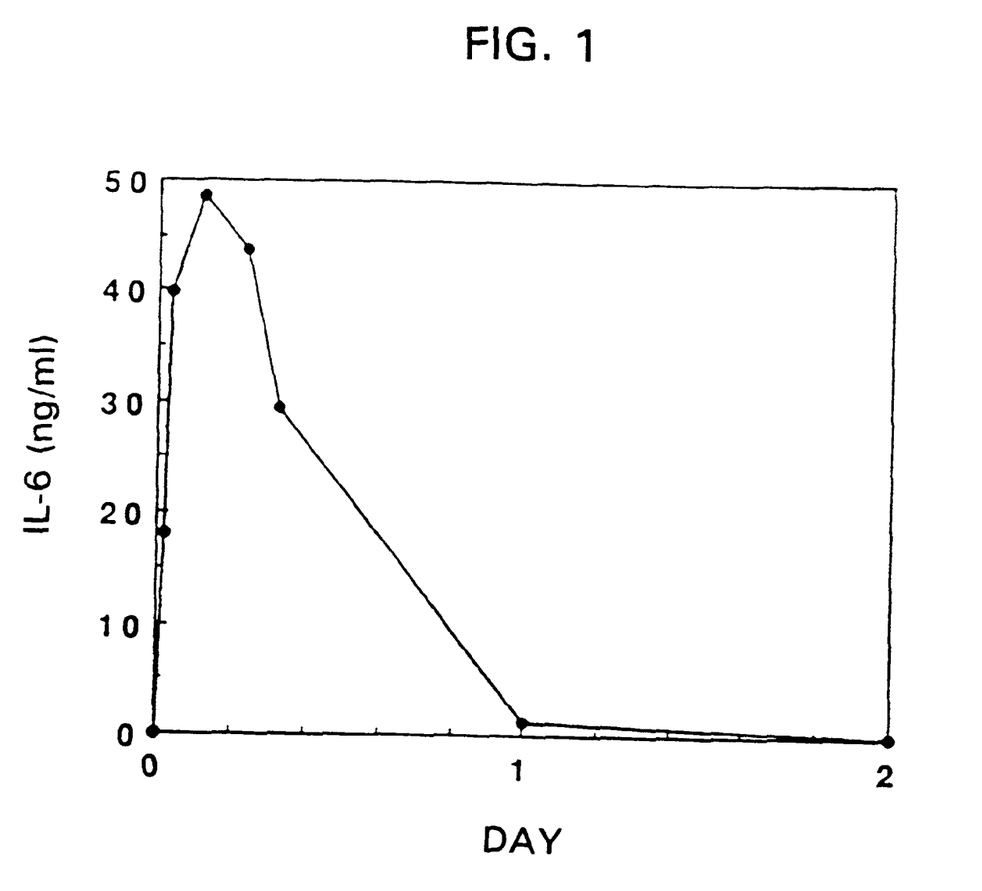
FIG. 1 is a graph of plasma concentrations of IL-6.

Injection of a single subcutaneous dose of 100 µg/kg of rh-IL-6 led to a rapid increase of plasma concentrations of IL-6 that persisted for 24 h (FIG. 1). Peak concentrations of up to 50 ng/ml were obtained at 3 h, whereafter IL-6 concentrations gradually declined to 1.3 ng/ml at 24 h corresponding to a terminal half life of 3–4 h. In the vehicle injected baboons, IL-6 concentrations remained below detection limit (<0.1 ng/ml) throughout the study.

Acute Phase Response

Figure 2A:
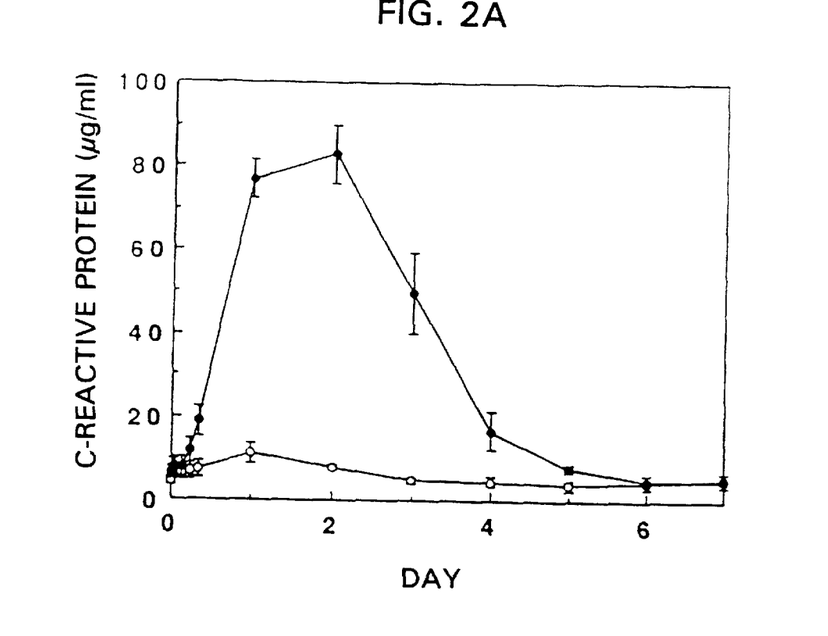
FIG. 2A is a graph of C-reactive protein concentrations.
Figure 2B:
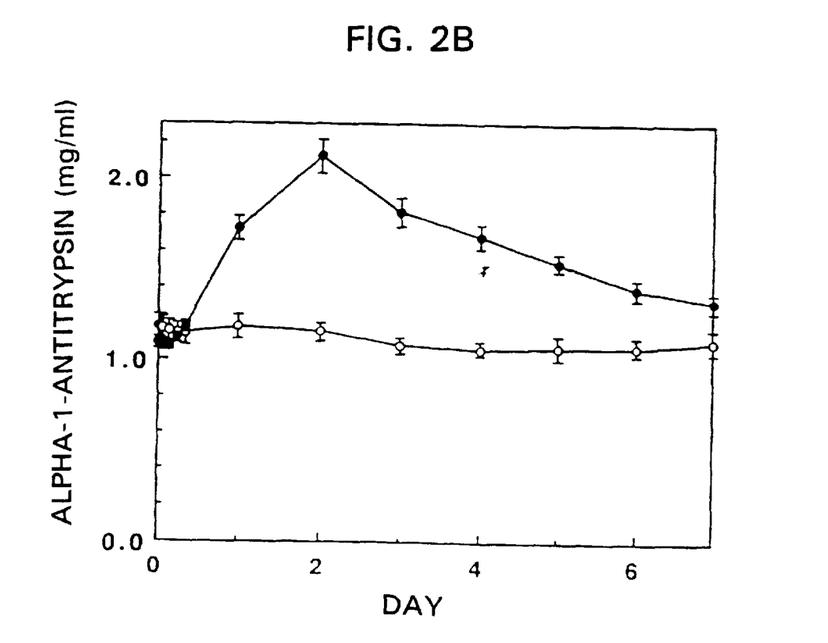
FIG. 2B is a graph of α-1-antitrypsin concentrations.
Figure 2C:
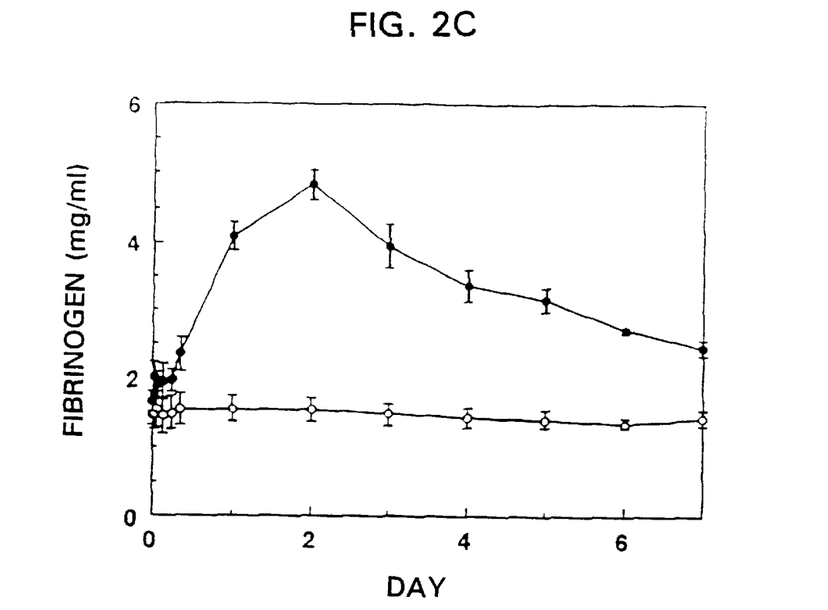
FIG. 2C is a graph of fibrinogen plasma concentrations.
Figure 2D:
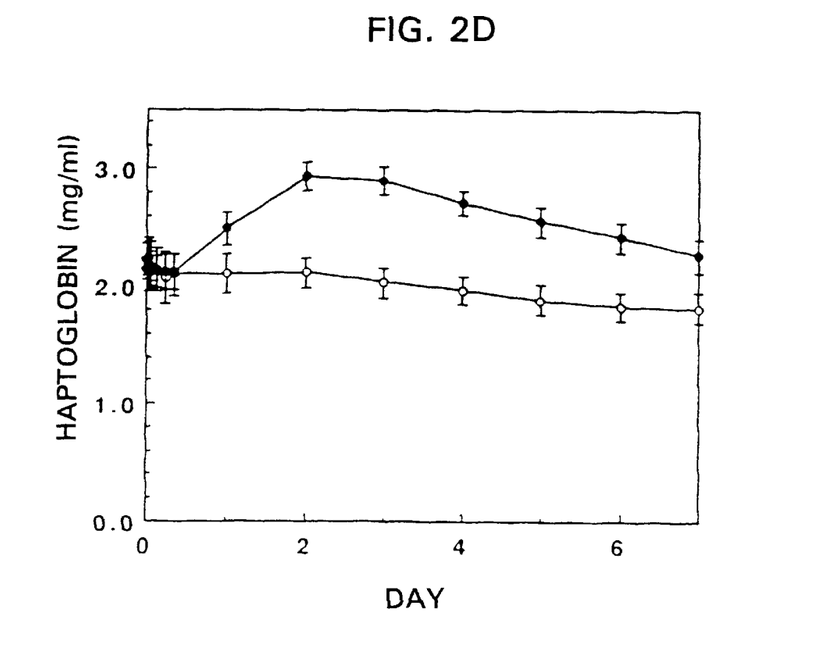
FIG. 2D is a graph of haptoglobin concentrations.
Figure 2E:
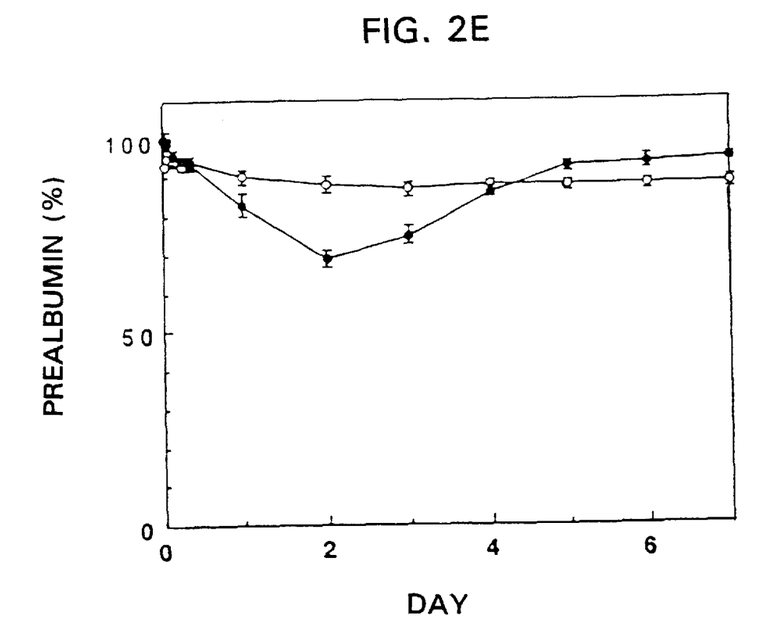
FIG. 2E is a graph of prealbumin concentrations.
Figure 2F:
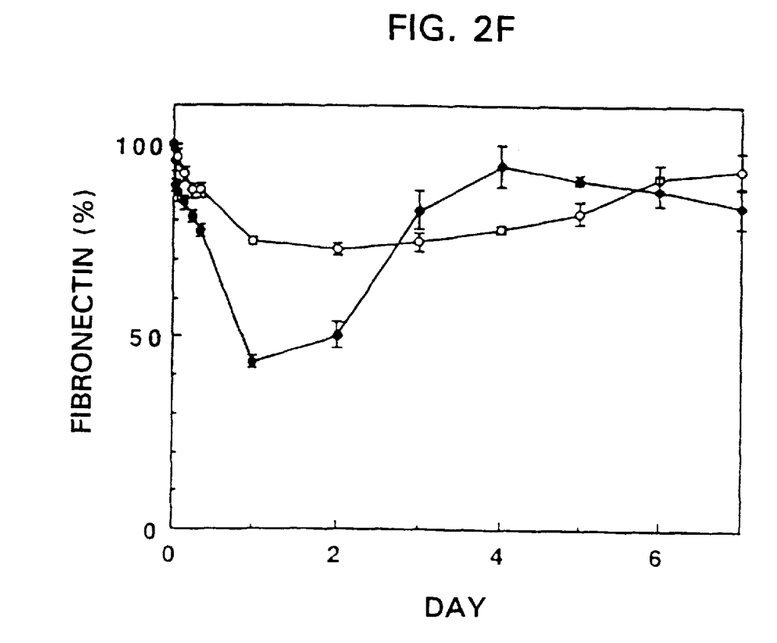
FIG. 2F is a graph of fibronectin concentrations.

To confirm that recombinant glycosylated human IL-6 is functional in baboons, we measured serum concentrations of several acute phase proteins. C-reactive protein concentrations increased up to eightfold with a maximum at day two after r-hIL-6 injection (FIG. 2A). Alpha-1-antitrypsin concentrations started to increase after a delay of 6 h and attained at day 2 maximal values that were twofold higher than in the controls (FIG. 2B). Also plasma concentrations of fibrinogen (FIG. 2C), haptoglobin (FIG. 2D), alpha-2-macroglobulin (not shown) and alpha-1-acid glycoprotein (not shown) significantly increased, whereas prealbumin and fibronectin concentrations transiently decreased (FIGS. 2E and F).

Coagulation System

Figure 3A:
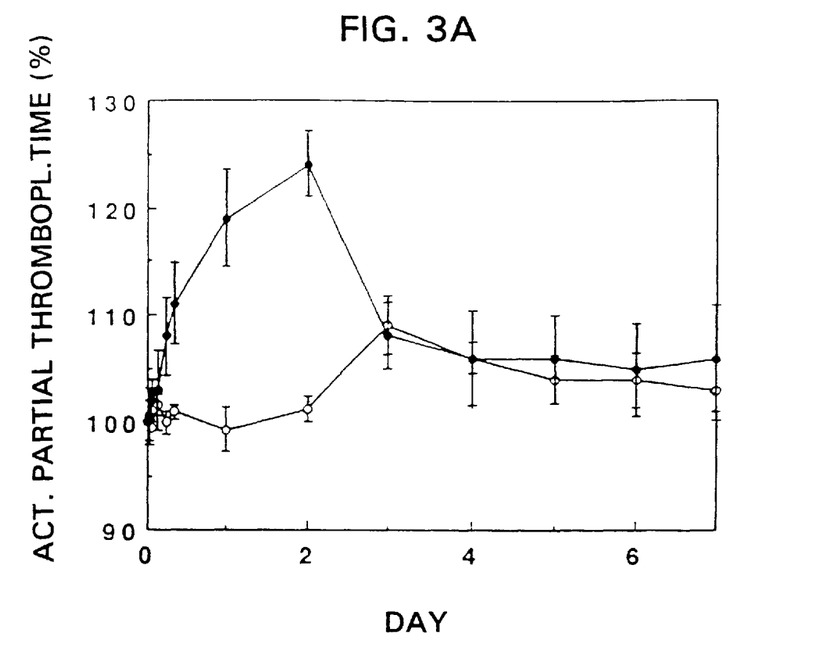
FIG. 3A is a graph of activated partial thromboplastin time.
Figure 3B:
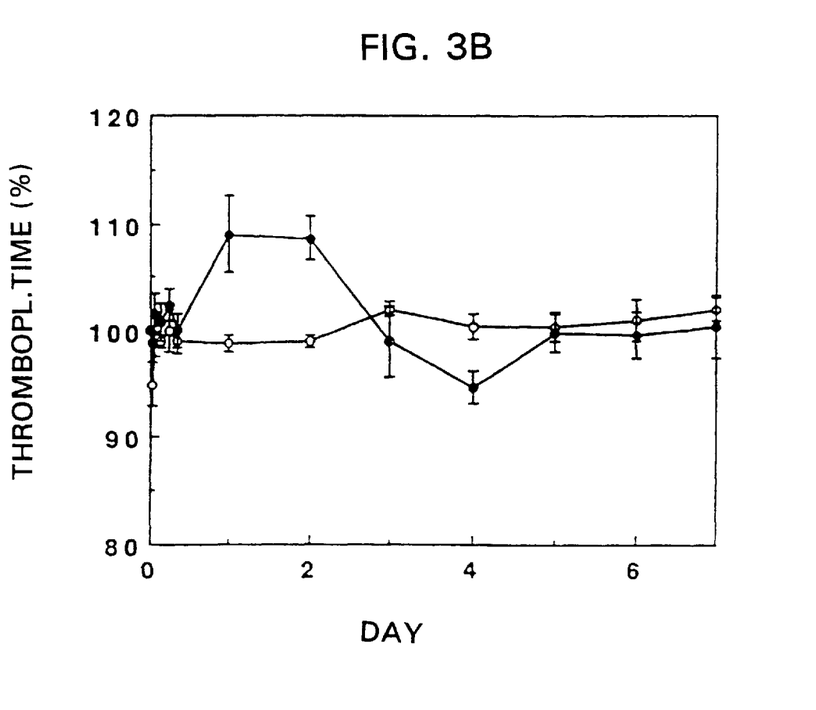
FIG. 3B is a graph of prothrombin time.
Figure 3C:
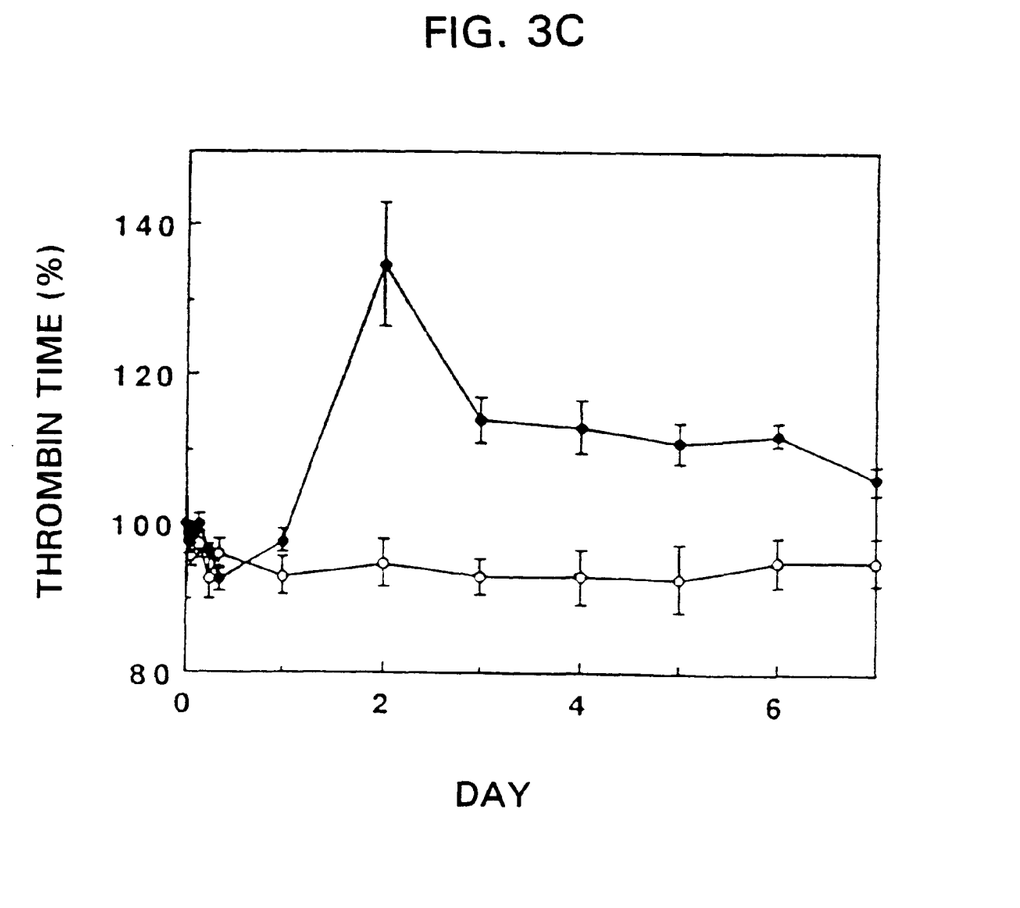
FIG. 3C is a graph of thrombin time.
Figure 4:
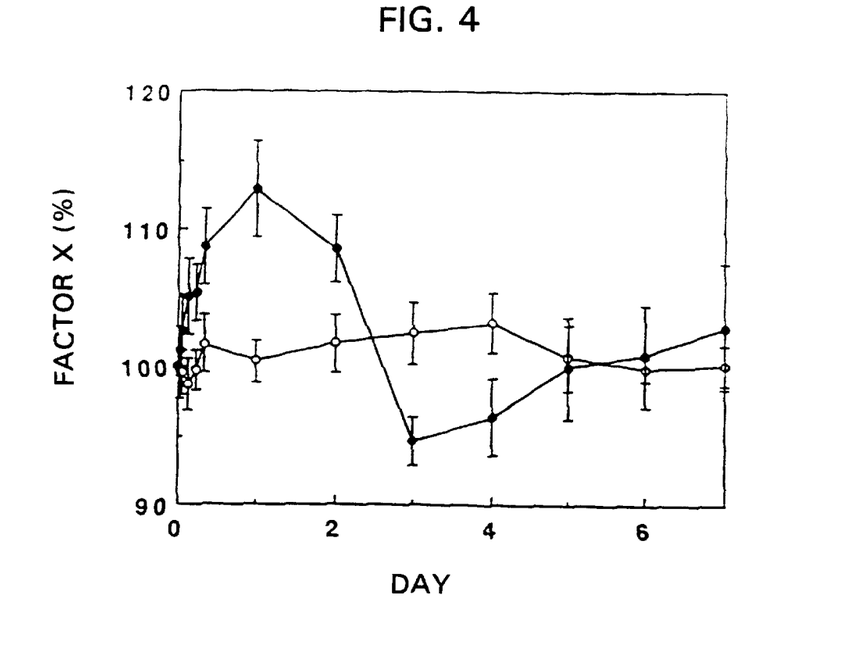
FIG. 4 is a graph of factor X activity.
Figure 5:
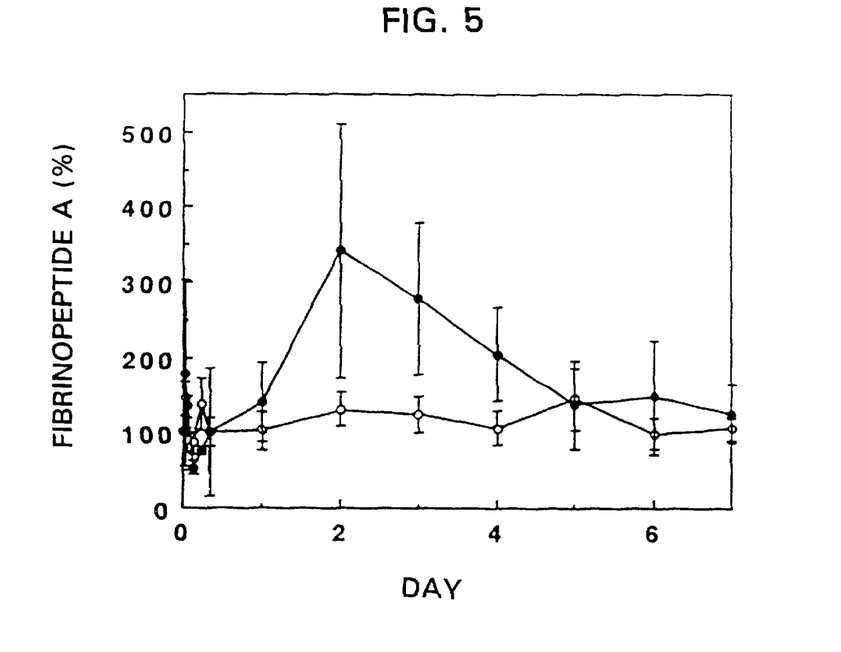
FIG. 5 is a graph of fibrinopeptide A levels.
Figure 6A:
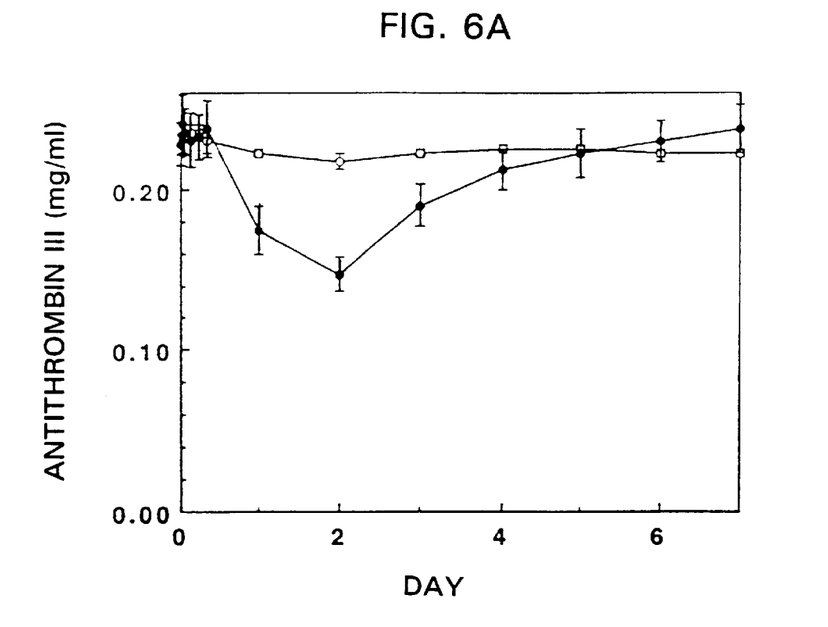
FIG. 6A is a graph of antithrombin III activity in mg/ml.
Figure 6B:
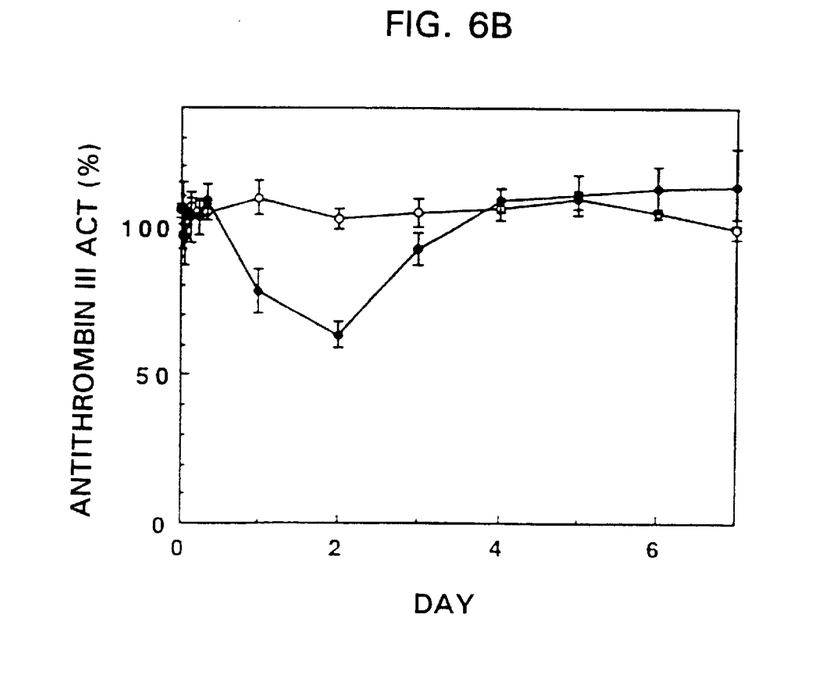
FIG. 6B is a graph of antithrombin III activity in percentage.
Figure 7:
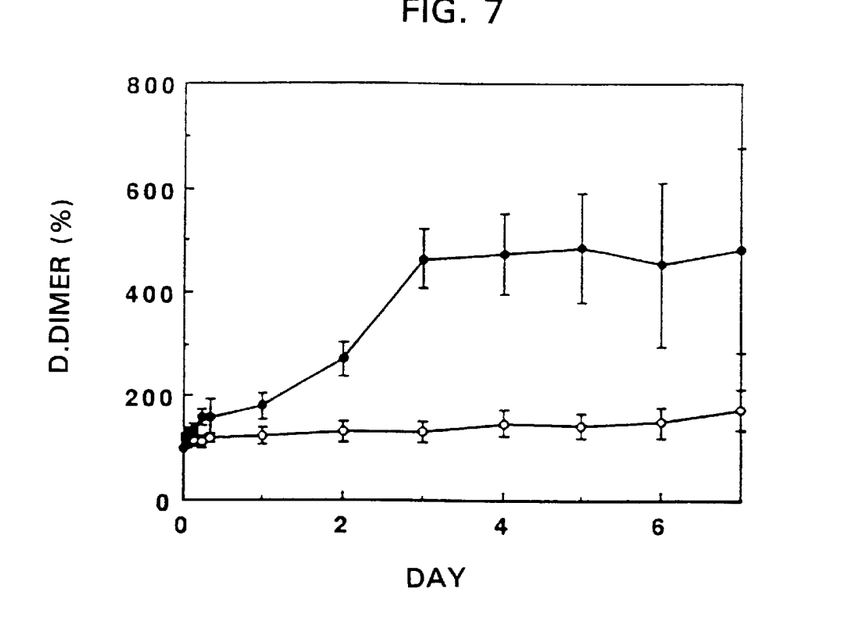
FIG. 7 is a graph of D-dimer concentrations.
Figure 8:
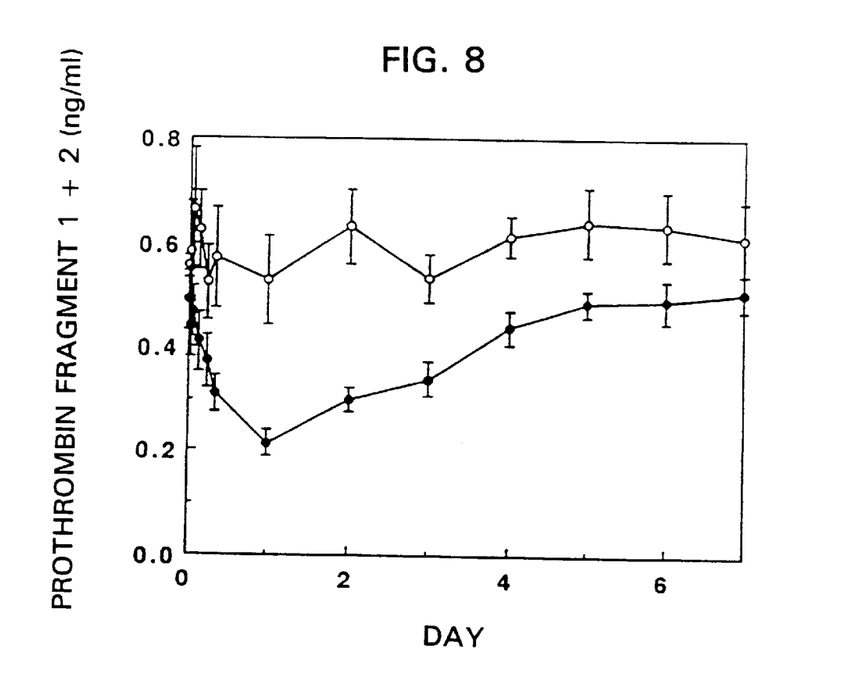
FIG. 8 is a graph of prothrombin fragment 1+2 concentrations.
Figure 9:
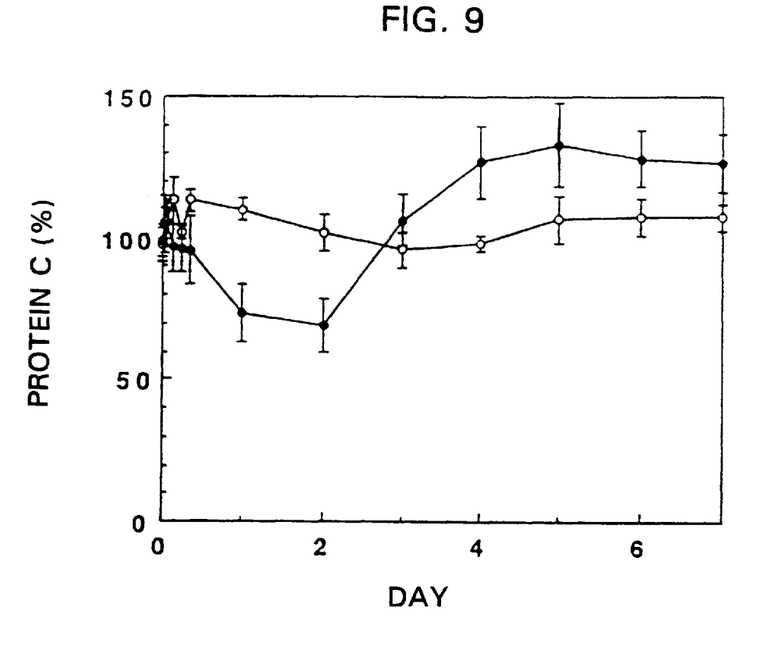
FIG. 9 is a graph of protein C concentrations.

Injection of rh-IL-6 led to marked effects on many parameters of the coagulation system. Significant increases in activated partial thromboplastin time, in prothrombin time and in thrombin time were observed after 1 to 3 days in the IL-6 treated baboons (FIG. 3). Functional activity measurements of factor X showed a decrease from day 1 to 3 (FIG. 4), whereas no modifications were observed in functional activity of prothrombin. Average fibrinopeptide A levels were more than twofold increased after 1 to 3 days (FIG. 5), whereas antithrombin III concentrations reached a nadir of 64% (FIG. 6). Most coagulation parameters returned to preinjection values at day 5. D-dimer concentrations started to increase after 24 h and reached in four days concentrations threefold higher than in the control group and remained elevated for at least seven days (FIG. 7). However, no significant changes in thrombin-antithrombin III complex concentrations were observed (data not shown). Prothombin fragment 1+2 concentrations decreased in the IL-6 treated baboons with a nadir at 24 h (FIG. 8). In the treated baboons, protein C concentrations decreased with a nadir at day two. Thereafter, protein C increased to values slightly higher than control values. In the control baboons protein C concentrations remained constant (FIG. 9).

Fibrinolytic System

Figure 10:
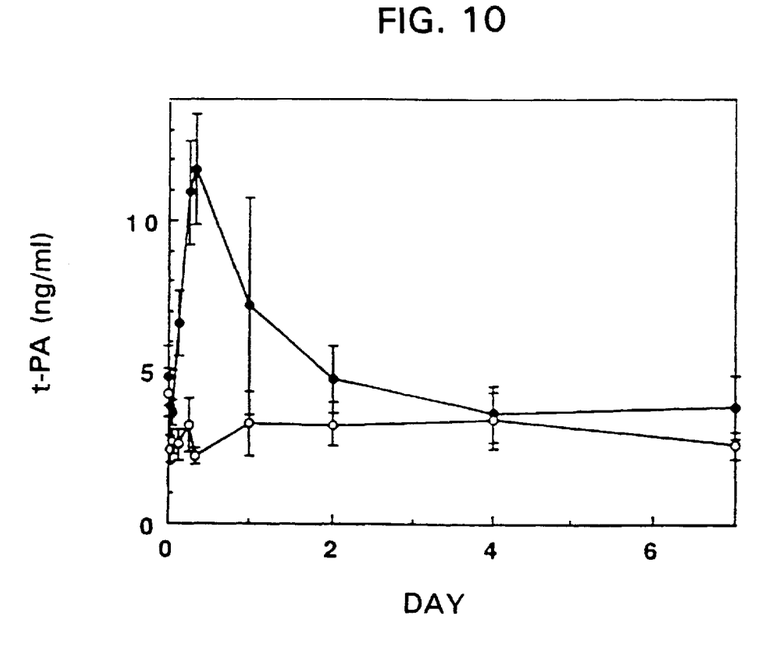
FIG. 10 is a graph of t-PA concentrations.
Figure 11:
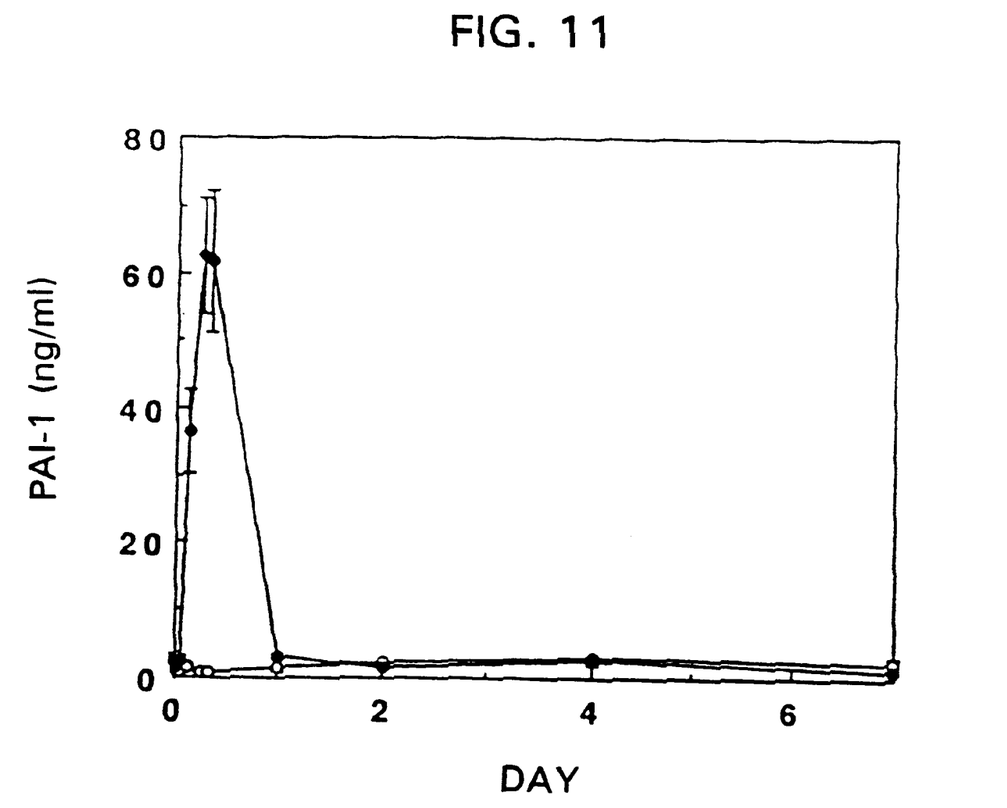
FIG. 11 is a graph of PAI-1 concentrations.

The injection of rh-IL-6 had profound effects on t-PA and PAI-1 concentrations in the baboons. t-PA concentrations increased after a delay of 3 h and attained after 6 to 8 h maximal values that were up to fourfold higher than in the controls, whereafter t-PA concentrations gradually returned to normal (FIG. 10). PAI-1 concentrations increased with a pattern similar to that of t-PA, reached a maximum after 6–8 h that was thirtyfold higher than in the controls and returned to normal within 24 h (FIG. 11).

Plasma concentrations of plasmin-antiplasmin complexes did not change after injection of IL-6 (not shown).

We claim:

1. A method of treatment or prophylaxis of a human or animal subject suffering from or at risk to a disorder selected from the group consisting of defibrination syndrome and consumptive coagulopathy wherein an effective dose of interleukin-6 is administered to said subject.

2. A method of treatment or prophylaxis of a human or animal subject suffering from or at risk to a consumptive thrombohemorrhagic disorder characterized by a fibrinolytic state selected from the group consisting of defibrination syndrome and primary fibrinolysis wherein an effective dose of interleukin-6 is administered to said subject.

3. A method as claimed in claim 2 in which the thrombohemorrhagic disorder is disseminated intravascular coagulation.

4. A method as claimed in claim 2 in which the disorder is compensated disseminated intravascular coagulation, defibrination syndrome, primary fibrinolysis or microangiopathic thrombocytopenia.

5. A method as claimed in claim 2 which said disorder is caused by liberation of tissue factors, endothelial damage, vascular malformations and infections.

6. A method as claimed in claim 5 in which said infections are accompanied by septic shock.

7. A method as claimed in claim 2 which said interleukin-6 is in dosage unit form, each unit containing 35 to 350 $\mu$g of interleukin-6 per dose.

8. A method as claimed in claim 2 in which the interleukin-6 is administered intravenously at a dose level of 0.5 to 30 $\mu$g/kg body weight/day.

9. A method as claimed in claim 2 in which the interleukin-6 is administered parenterally or by a delayed release formulation at 0.02 to 1.25 $\mu$g/kg body weight/hour.

* * * * *